United States Patent
Li et al.

(10) Patent No.: US 10,347,477 B2
(45) Date of Patent: Jul. 9, 2019

(54) METHODS AND SYSTEMS FOR QUANTITATIVE MASS ANALYSIS

(71) Applicant: Thermo Finnigan LLC, San Jose, CA (US)

(72) Inventors: Linfan Li, San Jose, CA (US); Jae C. Schwartz, Gilroy, CA (US)

(73) Assignee: THERMO FINNIGAN LLC, San Jose, CA (US)

( * ) Notice: Subject to any disclaimer, the term of this patent is extended or adjusted under 35 U.S.C. 154(b) by 0 days.

(21) Appl. No.: 15/911,304

(22) Filed: Mar. 5, 2018

(65) Prior Publication Data
US 2018/0277345 A1    Sep. 27, 2018

Related U.S. Application Data

(60) Provisional application No. 62/476,507, filed on Mar. 24, 2017.

(51) Int. Cl.
*H01J 49/00* (2006.01)
*H01J 49/42* (2006.01)
*G01N 27/62* (2006.01)

(52) U.S. Cl.
CPC .......... *H01J 49/0031* (2013.01); *G01N 27/62* (2013.01); *H01J 49/0081* (2013.01); *H01J 49/429* (2013.01); *H01J 49/4225* (2013.01); *H01J 49/0009* (2013.01)

(58) Field of Classification Search
CPC .............. H01J 49/0031; H01J 49/0081; H01J 49/0009; H01J 49/4225; G01N 27/62
USPC ................ 250/281, 282, 283, 288
See application file for complete search history.

(56) References Cited

U.S. PATENT DOCUMENTS

| | | | |
|---|---|---|---|
| 6,147,348 A | 11/2000 | Quarmby et al. | |
| 7,569,813 B2 | 8/2009 | Hager | |
| 7,692,142 B2 | 4/2010 | Schwartz et al. | |
| 8,258,462 B2 | 9/2012 | Remes et al. | |
| 8,415,617 B2 | 4/2013 | Schwartz | |
| 9,048,074 B2 | 6/2015 | Senko | |
| 9,911,588 B1 * | 3/2018 | Li | H01J 49/004 |
| 2005/0092910 A1 | 5/2005 | Geromanos et al. | |

(Continued)

FOREIGN PATENT DOCUMENTS

WO    2014208336 A1    12/2014

OTHER PUBLICATIONS

Schwartz et al., "A Two-Dimensional Quadrupole Ion Trap Mass Spectromter," J. Am. Soc. Mass. Spectrom., 13, 659-669, 2002.

*Primary Examiner* — Nicole M Ippolito
(74) *Attorney, Agent, or Firm* — A. J. Gokcek

(57) ABSTRACT

A method of quantitative mass analysis of precursor ion species of different mass-to-charge (m/z) ratios from the same or common ion injection event is disclosed. A plurality of precursor ion species with different respective m/z ratios are introduced into an ion trap mass analyzer at the same time. The precursor ion species are isolated. A first subset of the isolated precursor ions, which are multiply charged and have a first m/z ratio range, is fragmented and scanned by dividing the scan into at least two separate scan windows. A first mass spectrum is generated for the fragment ions of the first subset of precursor ions. A second subset of the isolated precursor ions having a second m/z ratio is fragmented and scanned, and a second mass spectrum is generated for the fragment ions of the second subset of precursor ions.

21 Claims, 6 Drawing Sheets

(56) References Cited

U.S. PATENT DOCUMENTS

| | | |
|---|---|---|
| 2005/0151073 A1 | 7/2005 | Kato |
| 2005/0253059 A1* | 11/2005 | Goeringer ........... H01J 49/0081 250/281 |
| 2011/0006200 A1 | 1/2011 | Loboda |
| 2011/0240844 A1 | 10/2011 | Ouyang et al. |
| 2012/0223223 A1 | 9/2012 | Sugiyama et al. |
| 2012/0305762 A1* | 12/2012 | Kaneko ................ H01J 49/427 250/283 |
| 2013/0009051 A1* | 1/2013 | Park ..................... H01J 49/063 250/282 |
| 2014/0131569 A1* | 5/2014 | Guna ................... H01J 49/004 250/284 |
| 2014/0339421 A1* | 11/2014 | Senko ................. H01J 49/0081 250/283 |
| 2014/0346345 A1* | 11/2014 | Makarov ............ H01J 49/0031 250/283 |
| 2014/0364337 A1 | 12/2014 | Hermanson et al. |
| 2016/0181077 A1 | 6/2016 | Ouyang et al. |
| 2016/0336163 A1 | 11/2016 | Remes et al. |

* cited by examiner

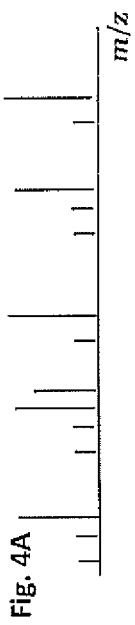
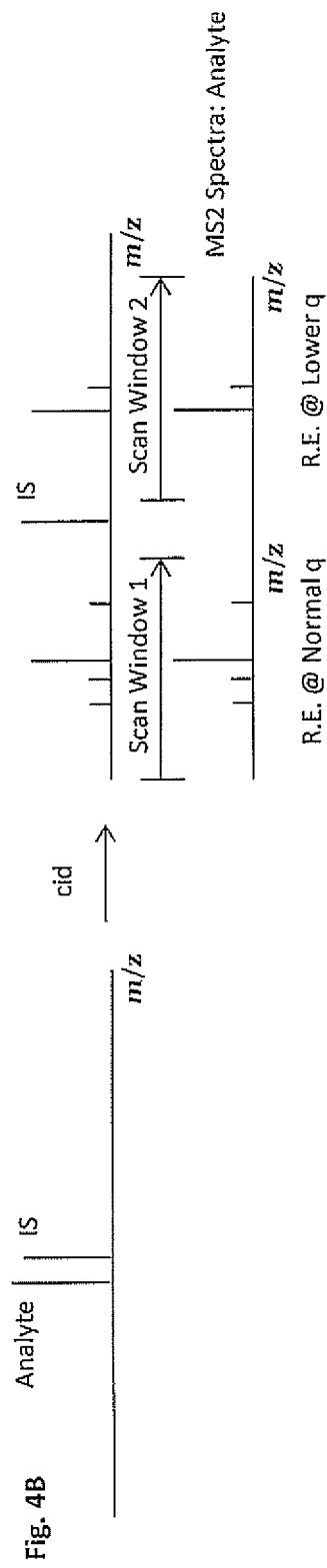
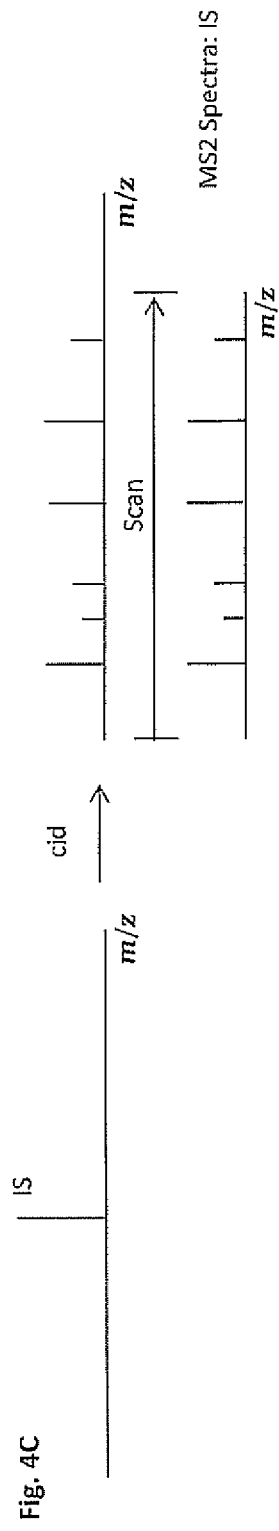
Fig. 4A
Fig. 4B
Fig. 4C

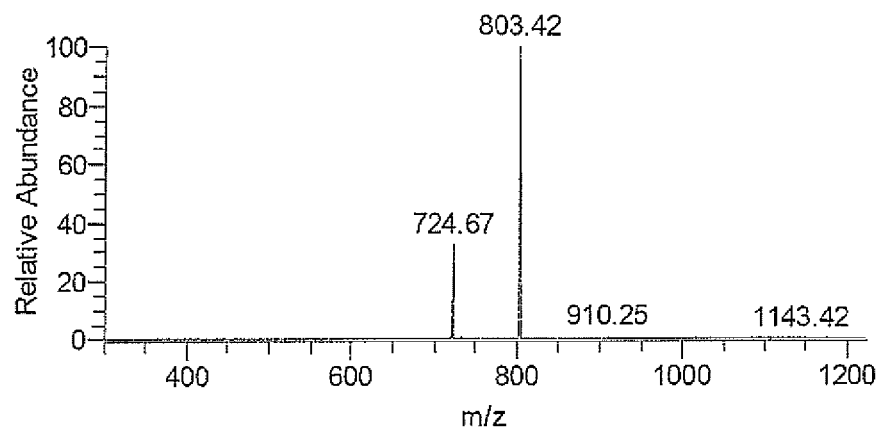
FIG. 5
FIG. 6A
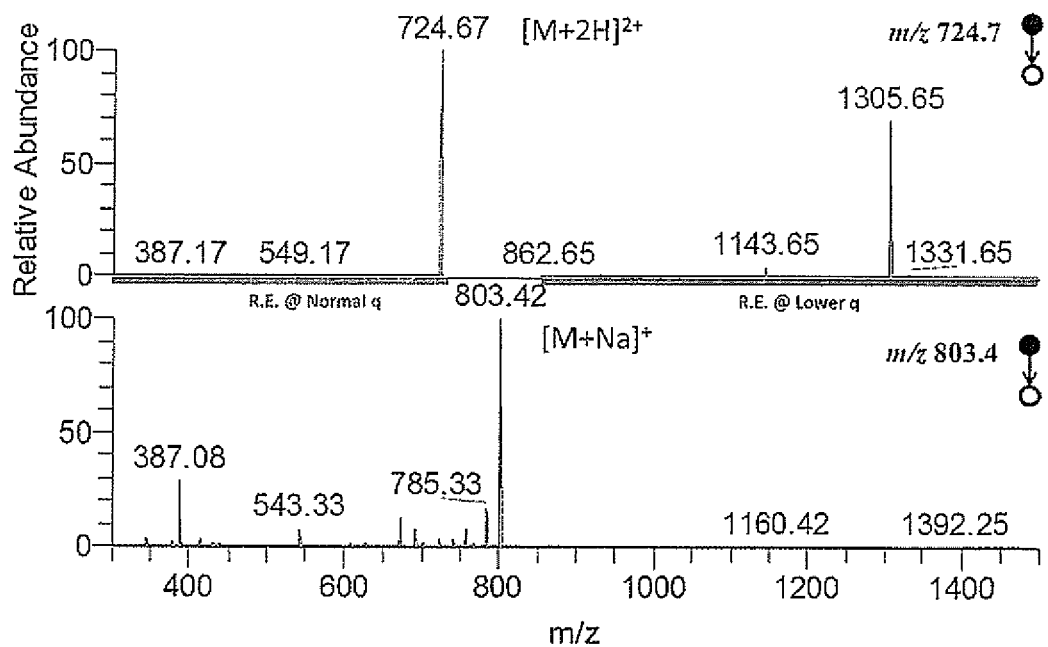
FIG. 6B

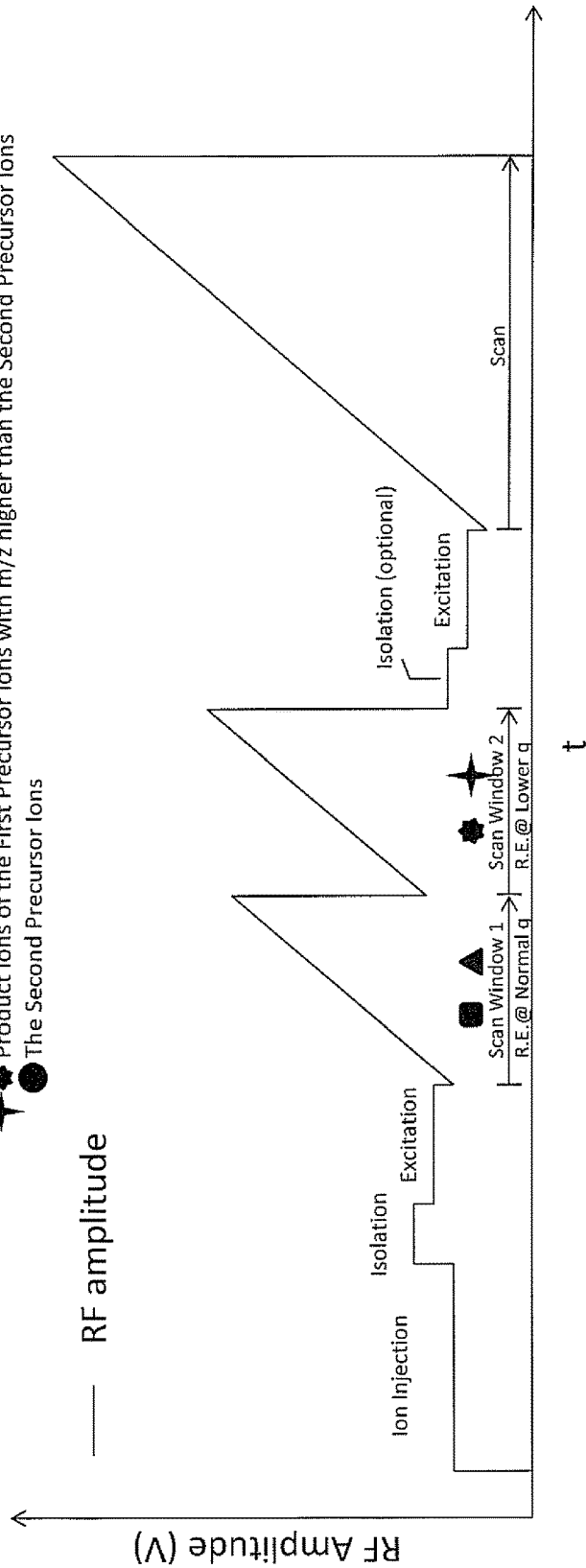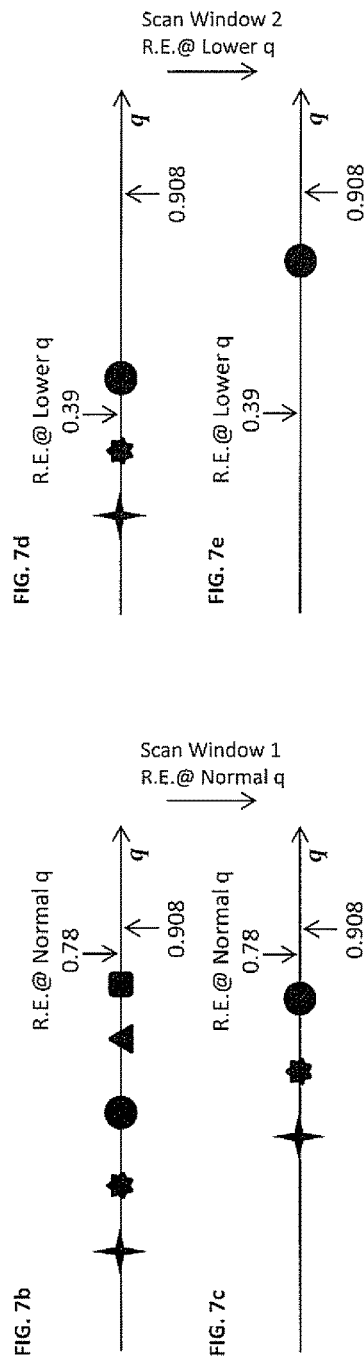

METHODS AND SYSTEMS FOR QUANTITATIVE MASS ANALYSIS

CROSS-REFERENCE TO RELATED APPLICATION

This application claims the priority benefit under 35 U.S.C. § 119(e) of U.S. provisional patent application No. 62/476,507 entitled "METHODS AND SYSTEMS FOR QUANTITATIVE MASS ANALYSIS" filed on Mar. 24, 2017, the disclosure of which is incorporated herein by reference.

FIELD OF THE INVENTION

This invention relates to mass spectrometry based quantitative analysis. More specifically, this invention relates to quantitative mass analysis of product ions dissociated from precursor species, some having multiple charge states, with different mass-to-charge (m/z) ratios injected into an ion trap mass analyzer in the same ion injection event.

BACKGROUND OF THE INVENTION

Conventional methods of quantitative mass analysis using ion trap mass spectrometers require the analyte and corresponding internal standard ions to be injected and analyzed from two time-separated ion injection events. Any fluctuations in the ionization process which occur in between those two ion injection events introduces inaccuracy in the quantitative mass analysis and subsequently leads to a bigger relative standard deviation (RSD) and therefore uncertainty in the measurement.

What is needed is a quantitative mass analysis method that minimizes or eliminates errors introduced by the fluctuations in the ionization process and improves the accuracy in the measurement.

SUMMARY

Embodiments of the present invention provide methods, systems, and apparatuses for quantitative mass analysis using ion trap mass analyzers. In one embodiment of the present invention, a method of operating an ion trap mass analyzer for quantification of analytes in a sample is provided. The analytes may comprise, in various implementations, therapeutic drugs or their metabolites, drugs of abuse or their metabolites, and endogenous substances such as creatinine. The method includes introducing sample ions into the ion trap mass analyzer. The sample ions, which are introduced into the ion trap in single or common ion injection events, include first precursor ions having a first mass-to-charge ratio (m/z) range and second precursor ions having a second m/z range. The first precursor ions are multiply charged. In some embodiments, both the first precursor ions and the second precursor ions are multiply charged. The method also includes concurrently isolating the first precursor ions and the second precursor ions and fragmenting (dissociating) the first precursor ions, but not the second precursor ions, to generate first product ions. The method further includes performing a first scan (alternately referred to as a first scan window) at a first value of a resonance ejection q (the value of the Mathieu parameter q at which resonance ejection occurs) to mass-selectively eject to a detector first product ions having m/z's lower than the second precursor ion m/z range, and performing a second scan (alternately referred to as a second scan window) at a second value of the resonance ejection q, lower than the first value, to mass-selectively eject to the detect first product ions having m/z's greater than the second precursor m/z range. By reducing the value of the resonance ejection q in the second scan, the low mass cut off (LMCO) may be maintained throughout the second scan at a value below the m/z of the second precursor ions, such that the second precursor ions do not develop unstable trajectories and are thereby retained in the trap for subsequent analysis. The method also includes fragmenting the second precursor ions to generate second product ions and performing a third scan to mass-selectively eject to the detector second product ions. In some embodiments, the third analytical scan of the second product ions can also be divided into at least two separate scan windows.

In some embodiments, the first precursor ions are analyte precursor ions and the second precursor ions are internal standard precursor ions. In other embodiments, the first precursor ions are internal standard precursor ions and the second precursor ions are analyte precursor ions. The internal standard may be, but is not limited to, an isotopologue of the analyte.

The amount of the analyte in the sample may be determined using a relationship between intensities of the product ions in the first mass spectrum and the second mass spectrum. In one specific embodiment, the first resonance ejection q value is approximately 0.78 and the second resonance ejection q value is approximately 0.30.

A multi-notched broadband excitation waveform may be applied to concurrently isolate the first precursor ions and the second precursor ions from any background ions.

The ions may be fragmented using collision-induced dissociation (CID). When using CID, an excitation waveform with a frequency which corresponds to or matches a secular frequency of the first precursor ions, but does not correspond to a secular frequency of the second precursor ions is applied, creating a resonance condition by which the first precursor ions pick up kinetic energy from the resonant field and undergo energetic collisions with molecules of a background gas and, causing dissociation. Also, after the first mass spectrum is acquired, an excitation waveform with a frequency which corresponds to or matches a secular frequency of the second precursor ions is applied, creating a resonance condition by which the second precursor ions pick up energy from the resonant field and undergo energetic collisions with molecules of a background gas, causing dissociation.

In another embodiment of the present invention, a method of operating an ion trap mass analyzer for quantification of analytes in a sample is provided. The analytes may comprise, in various implementations, therapeutic drugs or their metabolites, drugs of abuse or their metabolites, and endogenous substances such as creatinine. The method includes introducing sample ions into the ion trap mass analyzer. The sample ions, which are introduced into the ion trap in a single or common ion injection event, include first precursor ions having a first mass-to-charge ratio (m/z) range and second precursor ions having a second m/z range. The first precursor ions are multiply charged. In some embodiments, both the first precursor ions and the second precursor ions are multiply charged. The method also includes isolating the first precursor ions and the second precursor ions and fragmenting the first precursor ions, but not the second precursor ions, to generate first product ions of m/z above and below the second m/z range of the second precursor ions. The method further includes performing a first mass analysis scan divided into at least two separate scan windows to mass-selectively eject and detect the first product ions to acquire a first mass spectrum of the first product ions, while the second precursor ions are retained in the ion trap. In the at least two separate scan windows, the low-mass cut-off (LMCO) is lower than the m/z of the second precursor ions. The first mass analysis scan comprises performing resonance ejections at different q-values in each scan window, while the low-mass cut-off (LMCO) is kept below the m/z of the second precursor ions. In each scan window, the product ions are scanned out at different resonance ejection q-values and detected. The RF amplitude is scanned from low mass value product ions to high mass value product ions. The method also includes fragmenting the second precursor ions to generate second product ions and performing a second scan to mass-selectively eject and detect the second product ions and acquire a second mass spectrum of the second product ions. The amount of the analyte in the sample may be determined using a relationship between intensities of the product ions in the first mass spectrum and the second mass spectrum.

In another embodiment of the present invention, an ion trap mass spectrometer system adapted for quantitative mass analysis of precursor species is provided. The mass spectrometer includes an ion source configured so as to generate a plurality of precursor ion species having different respective mass-to-charge ratios (m/z). The mass spectrometer also includes an ion trap mass analyzer positioned to receive the precursor ions. The precursor ions include first precursor ions having a first m/z range and second precursor ions having a second m/z range. The first precursor ions are multiply charged. In some embodiments, both the first precursor ions and the second precursor ions are multiply charged. The ion trap mass analyzer has a controller which is programmed with instructions to cause the ion trap mass analyzer to perform steps of: concurrently isolating the first precursor ion species and the second precursor ions; fragmenting the first precursor ions, but not the second precursor ions, to generate first product ions of m/z above and below the second m/z of the second multiply-charged precursor ions; performing a first scan divided into at least two separate scan windows to mass-selectively eject and detect the first product ions and acquire a first mass spectrum of the first product ions, while retaining in the ion trap the second precursor ions, by performing resonance ejections at different q-values in each scan window, while the low-mass cut-off (LMCO) is kept below the m/z of the second precursor ions; fragmenting the second precursor ions to generate second product ions; and performing a second scan to mass-selectively eject and detect the second product ions and acquire a second mass spectrum of the second product ions.

BRIEF DESCRIPTION OF THE DRAWINGS

FIG. 4A shows a mass spectrum of multiple precursor species of different m/z ratios from the same ion injection event.

FIG. 4B shows a mass spectrum of the multiply-charged precursor ions of the analyte (right spectrum) after the background ions are ejected in the process of ion isolation (left spectrum).

FIG. 4C illustrates, subsequent to the acquisition of the mass spectrum of the analyte precursor ions in FIG. 4B, a mass spectrum of the remaining internal standard precursor ions.

FIG. 5 shows isolated precursor ions of an immunosuppressant solution containing precursor ions of analyte Vancomycin [(M+2H)2+] and internal standard Digoxin [M+Na]+.

FIG. 6A shows the $MS^2$ spectrum of Vancomycin [(M+2H)2+] obtained in two RF scannings with different resonance ejection q-values using the embodiment of the present invention described in FIG. 4A-4B.

FIG. 6B shows the $MS^2$ spectrum of Digoxin [M+Na]+ obtained in one RF scanning described in FIG. 4C.

FIGS. 7a, 7b, 7c, 7d, and 7e illustrate a scan function of RF amplitude for practical implementation of an analytical scan to mass sequentially detect product ions having different mass-to-charge (m/z) ratios (FIG. 7a), and q stability axes or lines demonstrating how the q-values of the ions change during mass analysis of the product ions (FIGS. 7b, 7c, 7d, and 7e).

DETAILED DESCRIPTION OF EMBODIMENTS

Figure 1:
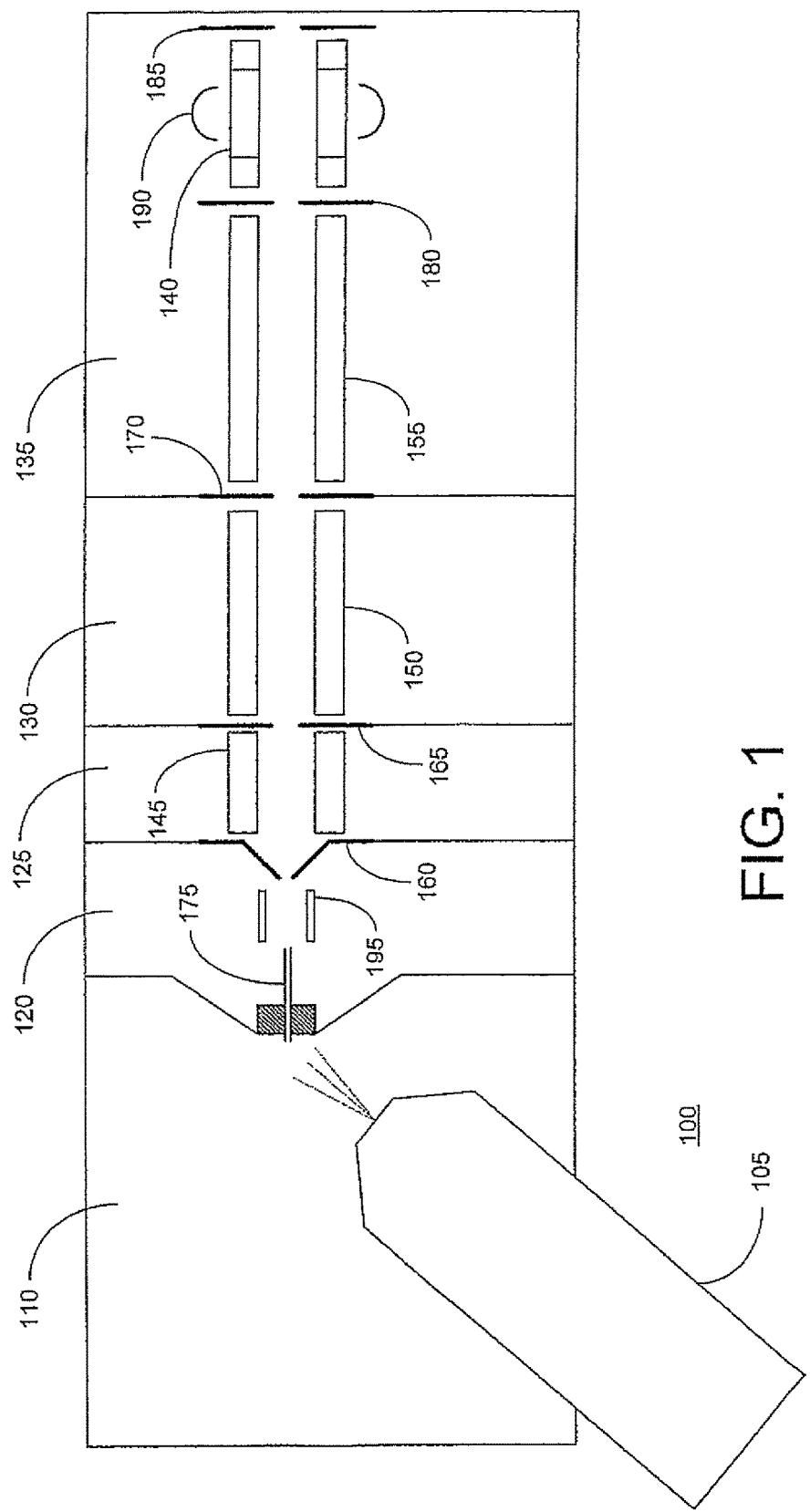
FIG. 1 is a schematic diagram of an ion trap mass spectrometer which may be operated in accordance with methods and systems embodying the present invention.

FIG. 1 illustrates an example of an ion trap mass spectrometer 100 which may be operated in accordance with embodiments of the present invention. It will be understood that certain features and configurations of mass spectrometer 100 are presented by way of illustrative examples, and should not be construed as limiting the methods of the present invention to implementation in a specific environment. An ion source, which may take the form of a conventional electrospray ion source 105, generates ions from a sample material. In other implementations, the ion source may take the form of a direct sampling ion source such as the Paper Spray ionization system available from Prosolia (Indianapolis, Ind.), in which a sample (e.g., a biological fluid such as blood or plasma) is deposited on a porous wicking material and electrosprayed from a tip of the material.

The ions are transported from ion source chamber 110, which for an electrospray source will typically be held at or near atmospheric pressure, through several intermediate chambers 120, 125 and 130 of successively lower pressure, to a vacuum chamber 135 in which ion trap 140 resides. Efficient transport of ions from ion source 105 to ion trap 140 is facilitated by a number of ion optic components, including quadrupole RF ion guides 145 and 150, octopole RF ion guide 155, skimmer 160, and electrostatic lenses 165 and 170. Ions may be transported between ion source chamber 110 and first intermediate chamber 120 through an ion transfer tube 175 that is heated to evaporate residual solvent and break up solvent-analyte clusters. Intermediate chambers 120, 125 and 130 and vacuum chamber 135 are evacuated by a suitable arrangement of pumps to maintain the pressures therein at the desired values. In one example, intermediate chamber 120 communicates with a port of a mechanical pump (not depicted), and intermediate pressure chambers 125 and 130 and vacuum chamber 135 communicate with corresponding ports of a multistage, multiport turbo-molecular pump (also not depicted). Ion trap 140 includes axial trapping electrodes 180 and 185 (which may take the form of conventional plate lenses) positioned axially outward from the ion trap electrodes to assist in the generation of a potential well for axial confinement of ions, and also to effect controlled gating of ions into the interior volume of ion trap 140 in order to regulate the filling (injection) time of ion trap 140; for example, DC offset voltages applied to axial trapping electrode 180 (and/or electrodes located upstream in the ion path relative to axial trapping electrode 180) may be set to selectively allow or block the flow of ions into ion trap 140. A damping/collision gas inlet (not depicted), coupled to a source of an inert gas such as helium or argon, will typically be provided to controllably add a damping/collision gas to the interior of ion trap 140 in order to facilitate ion trapping, fragmentation and cooling. Ion trap 140 is additionally provided with at least one set of detectors 190 (wherein each set may consist of a single detector or multiple detectors) that generate a signal representative of the abundance of ions ejected from the ion trap.

Ion trap 140, as well as other components of mass spectrometer 100, communicate with and operate under the control of a data and control system (not depicted), which will typically include a combination of one or more general purpose computers and application-specific circuitry and processors. Generally described, the data and control system acquires and processes data and directs the functioning of the various components of mass spectrometer 100. The data and control system will have the capability of executing a set of instructions, typically encoded as software or firmware, for carrying out the analysis methods described herein.

Figure 2:
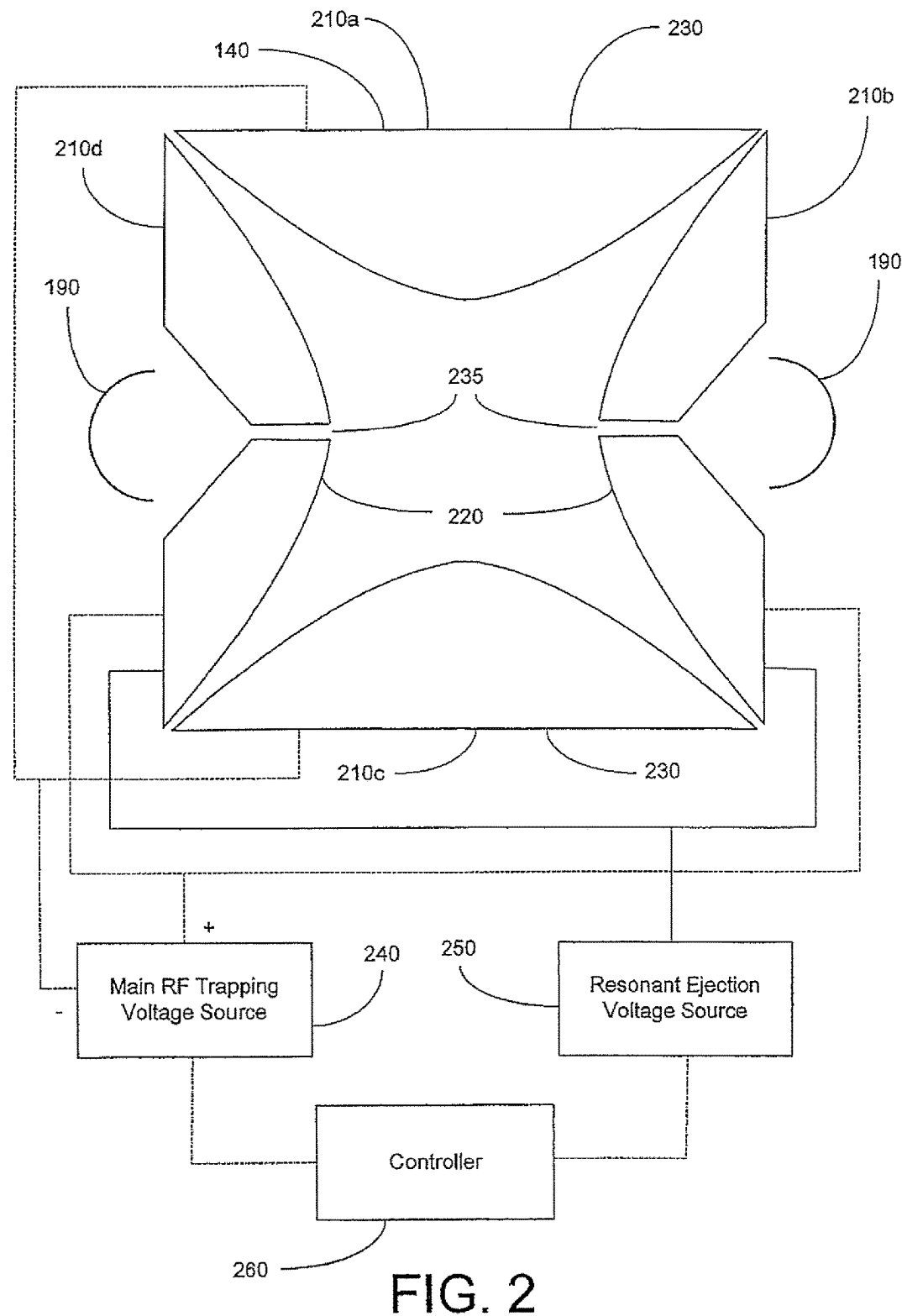
FIG. 2 is a lateral cross-sectional view of a two-dimensional radial ejection ion trap mass analyzer which may be used to implement methods and systems embodying the present invention.

FIG. 2 depicts a cross-sectional view of ion trap 140, which may be constructed as a conventional two-dimensional ion trap of the type described by Schwartz et al. in "A Two-Dimensional Quadrupole Ion Trap Mass Spectrometer", J. Am. Soc. Mass Spectrometry, 13: 659-669 (2002). Ion trap 140 includes four elongated electrodes 210*a*, 210*b*, 210*c*, 210*d*, each electrode having an inwardly directed hyperbolic-shaped surface, arranged in two electrode pairs 220 and 230 aligned with and opposed across the trap centerline. The electrodes of one electrode pair 220 are each adapted with an aperture (slot) 235 extending through the thickness of the electrode in order to permit ejected ions to travel through the aperture to an adjacently located detector 190. A main RF trapping voltage source 240 applies opposite phases of an RF voltage to electrode pairs 220 and 230 to establish an RF trapping field that radially confines ions within the interior of ion trap 140. During analytical scans, resonant ejection voltage source 250 applies an oscillatory voltage across apertured electrode pair 220 to create a dipole excitation field. The amplitude of the applied main trapping RF voltage is ramped such that ions come into resonance with the excitation field in order of their m/z's. The resonantly excited ions develop unstable trajectories and are ejected through apertures 235 to detectors 190. Control of the main RF trapping voltage, resonant ejection voltage, and CID excitation voltage applied to electrodes of ion trap 140, specifically adjustment of their amplitudes, is affected by a controller 260 that forms part of the data and control system.

While FIG. 2 depicts a conventionally arranged and configured two-dimensional ion trap, practice of the invention should not be construed as being limited to any particular ion trap geometry or configuration. In an alternative implementation, the ion trap may take the form of a symmetrically stretched, four-slotted ion trap of the type described in the U.S. Pat. No. 8,415,617 by Jae C. Schwartz and entitled "Two-Dimensional Radial-Ejection Ion Trap Operable as a Quadrupole Mass Filter", the disclosure of which is herein incorporated by reference. The ion trap may also constitute a part of a dual ion trap mass analyzer structure disclosed in U.S. Pat. No. 7,692,142 for "Differential-Pressure Dual Ion Trap Mass Analyzer and Methods of Use Thereof" by Jae C. Schwartz et al, which is also incorporated herein by reference. The methods described herein may also be utilized in connection with conventional rotationally symmetric three-dimensional ion traps (including variants such as toroidal or cylindrical ion traps) as well as for rectilinear ion traps.

Figure 3:
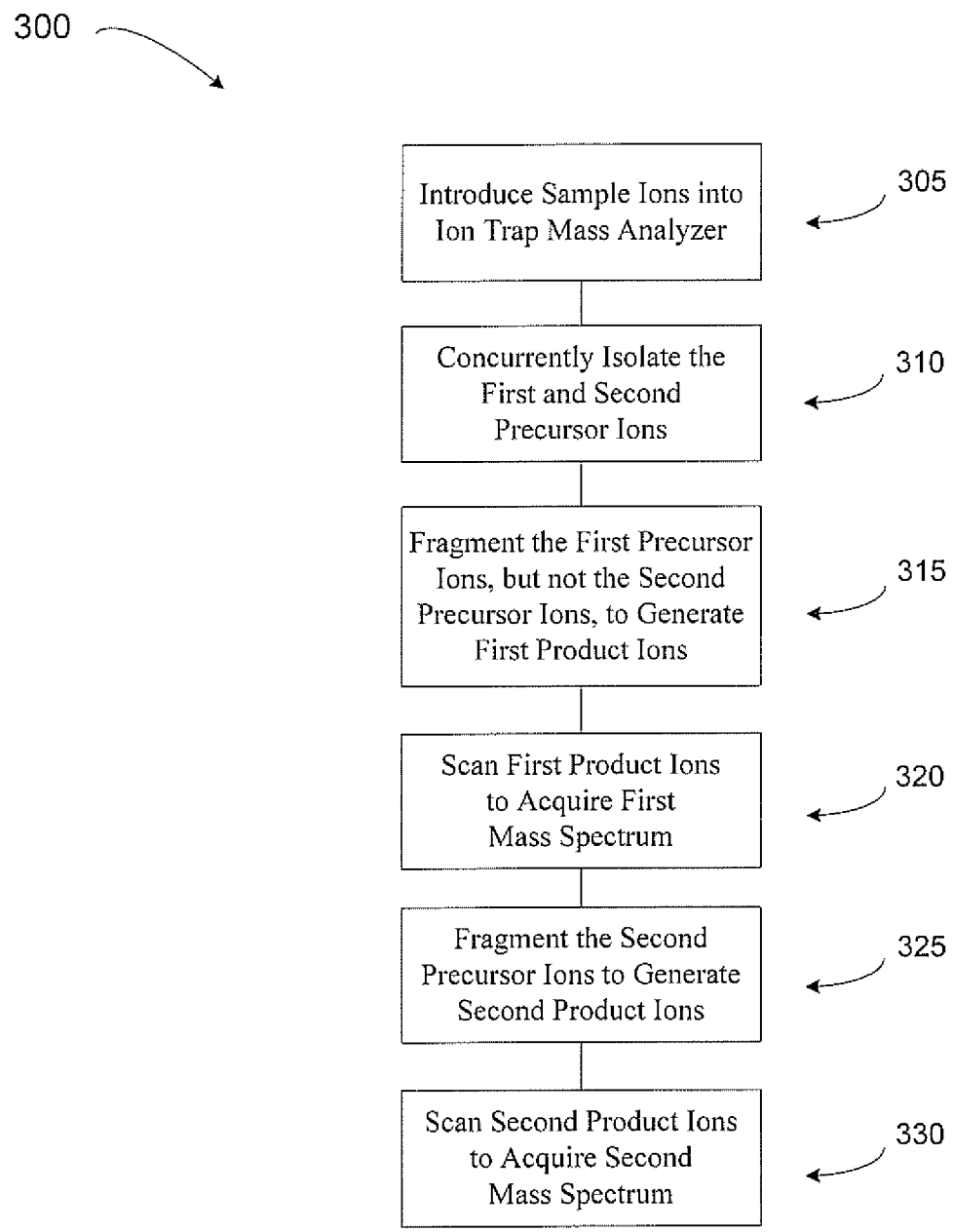
FIG. 3 is a flowchart depicting steps of a method of operating an ion trap mass analyzer for quantification of multiply-charged analytes in a sample, in accordance with one embodiment of the present invention.

FIG. 3 is a flowchart 300 depicting steps of a method of operating an ion trap mass analyzer for quantification of analytes in a sample, in accordance with one embodiment of the present invention. In certain implementations, the sample may take the form a biological fluid, such as blood, plasma, saliva, or urine, or fraction thereof, or an extract from a biological tissue sample. The analyte may comprise, for example, a therapeutic drug or its metabolite, a drug of abuse or its metabolite, or an endogenous substance, such as creatinine or a steroid hormone. In step 305, sample ions, generated by the ionization source by ionizing molecules in the sample by an appropriate technique, are introduced into an ion trap mass analyzer. The sample ions include first precursor ions having a first m/z and second precursor ions having a second m/z, different from the first m/z. The first precursor ions are multiply charged. In one specific embodiment, the first precursor ions are analyte precursor ions, and the second precursor ions are internal standard precursor ions. As is known in the art, the internal standard from which the internal precursor ions are generated may consist of, but is not limited to, an isotopologue (e.g., a deuterated version) of the corresponding analyte. While the description set forth below discusses quantification of a single analyte, variants of this technique may quantify multiple analytes (e.g., a panel of two or more therapeutic drugs). Alternatively, the first precursor ions can be internal standard precursor ions, while the second precursor ions can be analyte precursor ions. In a preferred mode, the first precursor ions and the second precursor ions are introduced into the ion trap mass analyzer from a common injection event, i.e. the first and second precursor ions both enter the ion trap during a period defined by an injection start time (when the applied DC offset voltage(s) is/are set to allow the passage of ions into the ion trap) and an injection end time (when the applied DC offset voltage(s) is/are switched to a value that blocks the passage of ions into the ion trap).

Following the introduction of ions including the first and second precursor ions into the ion trap, the first precursor ions and the second precursor ions are isolated concurrently (step 310) by removing ions having m/z's other than those of the first and second precursor ions. As is known in the art, this operation is performed by applying oscillatory voltages to the ion trap electrodes to establish an electric field that kinetically excites the non-desired ions (those other than the first and second precursor ions) such that the excited ions are ejected from the ion trap or are neutralized via collisions with electrode surfaces. In one illustrative implementation, concurrent isolation of the first and second precursor ions is achieved by applying a notched multifrequency waveform voltage to the trap electrodes, as described in U.S. Pat. No. 9,048,074. In such waveforms, the frequency notches are set to correspond to the secular frequencies of the ions to be isolated, such that those ions are not kinetically excited. Next, in step 315, the first precursor ions, but not the second precursor ions, are fragmented to generated first product ions of m/z above and below the second m/z. Fragmentation may be carried out using collision induced dissociation (CID) by applying an excitation waveform with a frequency which closely matches a secular frequency of the first precursor ions but is sufficiently different from the secular frequency of the second precursor ions to avoid substantial resonant excitation thereof. In this manner, at least a portion of the first precursor ions undergo energetic collisions with atoms or molecules of collision gas (also referred to as background or damping gas), causing them to fragment into first product ions, whereas the second precursor ions remain substantially unfragmented.

Because the first precursor ions are multiply charged (e.g., cations carrying a charge of +2 or greater), the resultant product ions may include a first group having m/z's lower than that of the precursor ions (those product ions that retain the same charge state as the precursor) as well as a second group having m/z's higher than that of the precursor ions (those product ions having a reduced charge state relative to the precursor ions). Generally, performing a single analytical scan to acquire a product ion spectrum including both the low-m/z group and the high-m/z group would result in the ejection from the ion trap of the second precursor ions, which will typically have an m/z within the range spanned by the product ions. To enable retention of the second precursor ions in the ion trap for subsequent analysis a multi-scan window approach may be employed, as described below.

Next, in step 320, a first analytical scan is performed by dividing the scan into at least two separate scan windows to mass-selectively eject and detect the first product ions to the detector of the ion trap mass analyzer and thereby acquire a first mass spectrum of the first product ions, while retaining the second precursor ions in the ion trap. In the first scan window, a resonance ejection scan is performed by gradually increasing the RF trapping voltage amplitude while applying an oscillatory resonance ejection voltage to trap electrodes. For this scan window, the resonance ejection q-value may be set to a "normal" (i.e., typical) value of approximately 0.78. As is known in the art, the resonance ejection q-value is determined by the frequency of the applied oscillatory resonance ejection voltage. The RF trapping voltage amplitude ramp is terminated at a point at which the Mathieu parameter q of the second precursor ions is below the resonance ejection q, such that the second precursor ions are not resonantly ejected. After completion of the first scan window, the RF trapping voltage is reduced and a resonance ejection scan is performed in a second scan window to eject the higher-m/z product ions. The resonance ejection scan for the second window is performed at a reduced resonance ejection q value relative to the first scan window (by appropriately adjusting the frequency of the resonant ejection voltage applied to the trap); for example, if the resonance ejection q value for the first scan window is fixed at 0.78, the scan for the second scan window may be performed at a resonance ejection q-value between approximately 0.05 to approximately 0.77 By reducing the resonant ejection q-value in the second scan window, the q for the second precursor ions is maintained throughout the scan at a value less than the Mathieu instability limit of 0.908 (but above the resonant ejection q-value), thereby avoiding ejection of the second precursor ions from the trap. Otherwise expressed, reduction of the resonant ejection q-value maintains the LMCO for all times during the RF trapping amplitude ramp at a value below the m/z of the second precursor ions. The effect of the scanning of the RF amplitude in step 320 may be more easily understood with reference to the graph appearing in FIG. 7a and the q stability axes (lines) demonstrating how the q-values of the ions change during a mass analysis of the product ions (FIGS. 7b-7e). After ion injection and isolation for the first and second precursor ions, and the excitation of the first precursor ions, the first product ions and the second precursor ions are confined in the ion trap at the same time as shown in FIG. 7b. By performing a resonance ejection (R.E.) at a normal R.E. q value, the first product ions with m/z values lower than the m/z value of the second precursor ions are resonantly ejected and detected in scan window 1 as shown in FIG. 7c. The first product ions with m/z values higher than the m/z value of the second precursor ions and the second precursor ions are still retained in the trap. After lowering the trapping RF amplitude, the q values of the retained ions are lowered as shown in FIG. 7d. The resonance ejection at a lower q value is performed to eject the first product ions of m/z values higher than the second precursor ions in scan window 2 as shown in FIG. 7e. The R.E. q value must be lower than the q value of the second precursor ions in the overall scan window 2.

The amplitude of the trapping RF voltage imposes an LMCO, which is given by $$LMCO = \frac{m}{z} * \frac{q}{0.908}$$

where, m/z is the mass to charge ratio of an ion species while q is the q value of this ion species. Thus, the LMCO will be lower than the m/z value as long as the q value is kept lower than 0.908 by controlling the RF amplitude. In all the ion manipulations discussed above, the second precursor ions are not resonantly ejected nor do they fall below the LMCO. Thus, the second precursor ions are still retained in the ion trap.

Subsequent to the acquisition of the mass spectrum of the lower m/z precursor ions, the second precursor ions (of higher m/z), which were retained in the ion trap mass analyzer, are fragmented in step 325 to generate second product ions. In one embodiment, fragmentation is carried out using CID by applying an excitation waveform with a frequency that closely matches a secular frequency of the second precursor ions, creating a resonance condition by which the second precursor ions pick up energy and collide with molecules of a background gas and dissociate.

Next, in step 330, a second analytical scan is performed to mass-selectively detect the second product ions and acquire a second mass spectrum that includes the second product ions. The selections of R.E. q value for analyzing the second product ions (of the second precursor ions) are quite flexible. A standard one window scan can be performed with one normal R.E. q value. Alternatively, a dual or multi window scan can be performed with same or different R.E. q values in each window. Any q values can be used in analyzing the second product ions, from about ~0.1 to about 0.9. It should also be noted that The R.E. q value for the second product ions are independent from the R.E. q values for the first product ions.

The results of the foregoing method steps are illustrated by the spectra depicted in FIGS. 4A-4C. FIG. 4A shows a depiction of precursor species of different m/z ratios introduced into an ion trap mass analyzer from the same ion injection event. In this example, the precursor ions include multiply-charged analyte ions which are of lower m/z compared to the corresponding internal standard ("IS") ions. FIG. 4B illustrates $MS^2$ analysis of the precursor ions of the analyte. First, ions other than those of the targeted analyte species and its corresponding internal standard are ejected in the process of ion isolation, as shown on the left side of FIG. 4B. As discussed above, a notched multifrequency waveform can be used to isolate the precursor ion species. In one embodiment, the analyte precursor ions and the internal standard precursor ions are concurrently isolated within an ion trap mass analyzer using a notched multifrequency waveform having frequency notches corresponding to the secular frequencies of the analyte and internal standard precursor ions, as is shown.

The analyte precursor ions are then selectively fragmented (for example, using the CID technique with the excitation frequency tuned to match the secular frequency of the analyte ions) and then analyzed by scanning the RF amplitude in at least two separate scan windows at resonance ejection q-values associated with the m/z of the first product ions to eject particular product ions of the analyte to a detector, while the precursor ions of the internal standard are trapped and intact. As discussed above, a RF amplitude corresponding to a LMCO below the m/z of the internal standard precursor ions is scanned in each scan window at resonance ejection q-values associated with the m/z of the analyte product ions. A mass spectrum is generated for the fragment ions of the analyte, as shown on the right side of FIG. 4B.

FIG. 4C illustrates, subsequent to the acquisition of the mass spectrum of the analyte precursor ions in FIG. 4B, mass analysis of product ions produced by fragmentation of the internal standard precursor ions. As shown on the left side of FIG. 4C, the analyte precursor ions have already been fragmented, analyzed and detected, leaving only the internal standard precursor ions. Next, the internal standard precursor ions are selectively fragmented by (for example) the CID technique and a MS' spectrum is generated for the fragment ions of the internal standard, as shown on the right side of FIG. 4C, by mass-selective ejection of ions to the ion trap detector.

As a result, spectra of the product ions of the multiply-charged analyte and the internal standard can be obtained using only a single ion accumulation step. The abundance of the product ions of the analyte and the internal standard can be used to calculate the ratio of analyte versus internal standard.

As is known in the art, the quantity of the analyte present in the sample may be calculated using a pre-calibrated relationship between the intensities of one or more characteristic product ions of the analyte appearing in the spectrum produced by the first analytical scan and the intensities of the corresponding characteristic product ions of the internal standard (which is added in a known quantity to the sample) appearing in the spectrum produced by the second analytical scan.

Experimental Section

The following examples are set forth to further describe embodiments and aspects of the present invention but are not to be construed as limiting the scope thereof.

FIG. 5 shows isolated precursor ions of an immunosuppressant solution containing precursor ions of analyte Vancomycin [(M+2H)2+] and internal standard Digoxin [M+Na]+. In this example, the solution contained 50 µg/ml of Vancomycin and 5 µg/ml of Digoxin, prepared in methanol/water (50/50) and infused to Nano-electrospray ionization (nanoESI) at a flow rate of 0.35 µl/min. A spray voltage of approximately 3 kV was applied to the solution. A dual-notch isolation waveform, which has a dual isolation window, was constructed and applied in the steps of ion injection and ion isolation. As shown in FIG. 5, precursor ions of analyte Vancomycin and internal standard Digoxin are isolated from any background ions. Precursor ions of lower m/z, doubly-charged ions of the analyte Vancomycin [(M+2H)2+], are firstly fragmented by collision induced dissociation (e.g., ion trap type resonant activated CID which is inherently m/z selective).

FIG. 6A show a $MS^2$ spectrum of Vancomycin [(M+2H) 2+] obtained in two RF scannings with different resonance ejection q-values. The product ions and un-dissociated precursor ions of the analyte Vancomycin of both lower and higher m/z than the internal standard precursor ions Digoxin [M+Na]+ are analyzed without destabilizing the internal standard precursor ions. After the acquisition of the $MS^2$ spectrum of precursor ions of the lower m/z analyte Vancomycin [(M+2H)2+] ions, the higher m/z internal standard precursor ions Digoxin [M+Na]+ are isolated (optional), fragmented, and scanned in one RF scanning as shown in FIG. 6B. By the end of the analysis, multiply-charged precursor ions of different m/z, introduced from the same ion injection event, can be analyzed respectively.

The advantages of the present invention include higher efficiency of sample utilization. Multiple precursor ions of different m/z and multiple charge states can be analyzed with a single ion injection event giving improved precision for quantitative measurements. Other advantages of the present invention include the ability to practice the invention on simple, low cost, hardware configurations such as a single linear ion trap mass spectrometer.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A method of operating an ion trap mass analyzer for quantification of analytes in a sample, comprising:
    a. introducing sample ions into the ion trap mass analyzer in a single injection event, the sample ions including first precursor ions having a first mass-to-charge ratio (m/z) range and second precursor having a second m/z range, the first precursor ions being multiply charged;
    b. concurrently isolating the first precursor ions and the second precursor ions;
    c. fragmenting the first precursor ions, but not the second precursor ions, to generate first product ions;
    d. performing a first scan at a first value of a resonance ejection q to mass-selectively eject to a detector first product ions having m/z's lower than the second precursor ion m/z range, and performing a second scan at a second value of the resonance ejection q, lower than the first value, to mass-selectively eject to the detector first product ions having m/z's greater than the second precursor ion m/z range, wherein the second precursor ions are retained in the ion trap mass analyzer during the first and second resonance ejection scans;
    e. fragmenting the second precursor ions to generate second product ions; and
    f. performing a third scan to mass-selectively eject to the detector second product ions.

2. The method of claim 1 wherein the first precursor ions are one of analyte precursor ions and internal standard precursor ions, and the second precursor ions are the other of analyte precursor ions and internal standard precursor ions.

3. The method of claim 2 further comprising determining an amount of the analyte using a relationship between intensities of the first and second product ions measured in steps (d) and (f).

4. The method of claim 1 further comprising applying a notched waveform to concurrently isolate the first precursor ions and the second precursor ions from any background ions.

5. The method of claim 1 wherein the fragmenting is carried out using ion trap collision-induced dissociation (CID).

6. The method of claim 1 wherein the resonance ejection q values in step (d) range from about 0.05 to about 0.90.

7. The method of claim 6 wherein the first resonance ejection q value is approximately 0.78 and the second resonance ejection q value is approximately 0.30.

8. A method of operating an ion trap mass analyzer for quantification of analytes in a sample, comprising:
   a. introducing sample ions into the ion trap mass analyzer in a single injection event, the sample ions including first precursor ions having a first mass-to-charge ratio (m/z) range and second precursor ions having a second m/z range, the first precursor ions being multiply charged;
   b. concurrently isolating the first precursor ions and the second precursor ions;
   c. fragmenting the first precursor ions, but not the second precursor ions, to generate first product ions of m/z above and below the second m/z;
   d. performing a first scan divided into at least two separate scan windows to mass-selectively eject and detect the first product ions and acquire a first mass spectrum of the first product ions, while retaining in the ion trap the second precursor ions, by performing resonance ejections at different q-values in each scan window, while the low-mass cut-off (LMCO) is kept below the m/z of the second precursor ions;
   e. fragmenting the second precursor ions to generate second product ions; and
   f. performing a second scan to mass-selectively eject and detect the second product ions and acquire a second mass spectrum of the second product ions.

9. The method of claim 8 wherein the first precursor ions are one of analyte precursor ions and internal standard precursor ions, and the second precursor ions are the other of analyte precursor ions and internal standard precursor ions.

10. The method of claim 9 further comprising determining an amount of the analyte in the sample using a relationship between intensities of the product ions in the first mass spectrum and the second mass spectrum.

11. The method of claim 8 further comprising applying a notched waveform to concurrently isolate the first precursor ions and the second precursor ions from any background ions.

12. The method of claim 8 wherein the fragmenting is carried out using ion trap collision-induced dissociation (CID).

13. The method of claim 8 wherein the ejection q-values range from about 0.05 to about 0.90.

14. The method of claim 13 wherein the first resonance ejection q-value is approximately 0.78 and the second resonance ejection q-value is approximately 0.30.

15. The method of claim 8 wherein the RF amplitude is scanned from low mass value product ions to high mass value product ions.

16. The method of claim 8 wherein performing the second scan comprises dividing the second scan into at least two separate scan windows to mass-selectively eject and detect the second product ions and acquire the second mass spectrum of the second product ions.

17. An ion trap mass spectrometer system for quantification of analytes in a sample, comprising:
   a. an ion source configured to generate sample ions, the sample ions including first precursor ions having a first mass-to-charge ratio (m/z) range and second precursor ions having a second m/z, the first precursor ions being multiply charged;
   b. an ion trap mass analyzer positioned to receive the sample ions, the ion trap mass analyzer having a controller being programmed with an algorithm comprising instructions to the ion trap mass analyzer to cause the ion trap mass analyzer to performs steps of: (a) concurrently isolating the first precursor ions and the second precursor ions; (b) to fragment the first precursor ions, but not the second precursor ions, to generate first product ions of m/z above and below the second m/z; (c) performing a first scan divided into at least two separate scan windows to mass-selectively eject and detect the first product ions and acquire a first mass spectrum of the first product ions, while retaining in the ion trap the second precursor ions, by performing resonance ejections at different q-values in each scan window, while the low-mass cut-off (LMCO) is kept below the m/z of the second precursor ions; (d) fragmenting the second precursor ions to generate second product ions; and (e) performing a second scan to mass-selectively eject and detect the second product ions and acquire a second mass spectrum of the second product ions.

18. The system of claim 17 wherein the first precursor ions are one of analyte precursor ions and internal standard precursor ions, and the second precursor ions are the other of analyte precursor ions and internal standard precursor ions.

19. The system of claim 18 wherein an amount of the analyte in the sample is determined using a relationship between intensities of the product ions in the first mass spectrum and the second mass spectrum.

20. The system of claim 17 wherein the ejection q-values range from about 0.05 to about 0.90.

21. The system of claim 17 wherein performing the second scan comprises dividing the second scan into at least two separate scan windows to mass-selectively eject and detect the second product ions and acquire the second mass spectrum of the second product ions.

* * * * *